United States Patent [19]

Wyton et al.

[11] 4,044,259
[45] Aug. 23, 1977

[54] METHOD AND APPARATUS FOR MONITORING THE FLOW OF SOLIDS

[75] Inventors: Wayne W. Wyton, Trail; Gerard Doeksen, Montrose, both of Canada

[73] Assignee: Cominco Ltd., Trail, Canada

[21] Appl. No.: 654,126

[22] Filed: Feb. 2, 1976

[51] Int. Cl.² ........................................... G01N 23/00
[52] U.S. Cl. ..................................................... 250/360
[58] Field of Search .................... 250/356, 358 R, 359, 250/360, 308

[56] References Cited

U.S. PATENT DOCUMENTS

| 2,953,682 | 9/1960 | Frank et al. | 250/308 |
| 3,518,425 | 6/1970 | Gruenwald | 250/360 |

*Primary Examiner*—Davis L. Willis

*Attorney, Agent, or Firm*—Arne I. Fors

[57] ABSTRACT

The flow of particulate solids through a screw conveyor or a screw feeder is monitored by passing radiant energy from a source in a generally vertical path into a bed of the solids flowing through the conveyor, receiving by a detector radiation that is not absorbed or scattered by the solids or the conveyor, and transmitting amplified electrical signals from the detector to a recorder. The detector extends parallel to the shaft of the conveyor screw for at least about one pitch length of the screw. The path of radiation from the source to the detector follows a plane that lies between the shaft and the conveyor casing on the lift side of the screw. Cyclic variations in radiation signals as tapered pitch-length segments of material move through the conveyor are averaged mechanically.

5 Claims, 2 Drawing Figures

METHOD AND APPARATUS FOR MONITORING THE FLOW OF SOLIDS

BACKGROUND OF THE INVENTION

This invention relates to an improved method and apparatus for monitoring the flow of particulate solids through a screw conveyor which employs a source of radiant energy and a radiation detector disposed so that radiation is passed into a bed of flowing solids in a conveyor and the portion of the radiation that is not absorbed or scattered by the solids or the apparatus is picked up by the detector, thereby energizing an electrical circuit connecting the detector and a recorder. Such apparatus is known as a nuclear weightometer.

U.S. Pat. No. 2,953,682 issued Sept. 20, 1960 to G. E. Frank et al. discloses use of radiant energy to detect changes in viscosity and mass of a liquid as it is stirred by rotation of a horizontal screw in a cylindrical reaction vessel. Radiation sources direct beams through both raised and depressed edges of liquid as it is being stirred by the screw. A change in the difference of the outputs of collectors in each radiation path indicates a change in viscosity. A change in the sum of the outputs indicates a change in mass. Elimination of the effect of random and periodic disturbances is provided by integration of readings obtained from the detector signals (Column 4, line 75 to Column 5, line 17).

In the process of U.S. Pat. No. 3,036,214 issued May 22, 1962 to R. C. Forney et al. radiant energy is used to indicate the progress of polymerization of liquid materials as it flows through a horizontal cylindrical chamber. The material is mixed by interrupted screw flights and intervening transverse screens. Viscosity changes, as indicated by relative vertical displacement of portions of the surface of the liquid at opposite sides of the vessel axis, are determined by beaming radiant energy, between two screw flights (Column 3, lines 54 to 66), to pass through part of the displaced liquid.

U.S. Pat. No. 3,518,425 issued June 30, 1970 to C. L. Gruenwald discloses nuclear radiation means for measuring the flow of solid material through a screw conveyor. The radiation source and detector of this patent are spaced to span the screw conveyor at right angles to the direction of flow of the solids. Both source and detector, which are parallel to one another, are substantially as long as the diameter of the conveyor. It is noted by the inventor that the orientation of the detector source relative to the free surface of the material in the screw is most significant. He demonstrates and claims orientation in which the signal transmitted from the detector to the recording means is linearized electronically more satisfactorily than it is in other positions, thereby recording more accurately the weight of material moving through the conveyor. The preferred orientation is obtained when the elongated source and elongated detector are supported in a plane transverse to the longitudinal extent of the screw conveyor, parallel to each other, and in a plane substantially perpendicular to the free surface of the material that is carried by the screw conveyor. As implied by the inventor's reference to U.S. Pat. No. 3,278,747 issued Oct. 11, 1966 to P. E. Ohmart and as shown in FIG. 1 therein, the radiation path spans only a small part of one pitch length of the conveyor screw.

In each of the foregoing nuclear detection means, only material in a narrow segment of one pitch length of the rotating screw is scanned. In the case of U.S. Pat. No. 3,518,425, the transverse radiation beam scans the full width of the screw conveyor with the result that the detector signal represents all the moving material that moves through the screw conveyor. Advantages of this arrangement are offset by the manner in which particulate material is moved in a screw conveyor. As a bed of this material is moved in a horizontal direction, it becomes deeper on the ascending side of the screw and it also climbs on the pushing surface of the screw blade, thus providing a depth differential along each screw pitch length. We have discovered that, by scanning the deeper portion of the material on the lift side of the screw for at least about a full pitch of the screw flight, the detector continuously receives a composite radiation signal from a representative portion of the material. A narrow transversely placed detector, as shown in the prior art, senses these variations in depth and provides a fluctuating signal that requires subsequent electronic averaging to eliminate irregular recording of uniform overall flow. These fluctuating signals are eliminated by the process and apparatus of the present invention.

STATEMENT OF INVENTION

In the monitoring of the flow of particulate material through a screw feeder or conveyor, in accordance with the present invention, we provide improved control of the effects on detector signals of periodic surface irregularities that are caused by rotation of the screw. We have observed that effective mechanical averaging of source to detector signal is obtained by an arrangement in which radiation from a source passes through a section of the screw feeder or conveyor that extends longitudinally for a distance at least about equal to the pitch of the screw. The detector is placed so that the path of radiation from the source to the detector does not pass through the shaft of the screw, thereby eliminating excessive absorption by the relatively large mass of metal in this part of the screw. It is important to place the source and detector with one above and one below a horizontal screw so that the radiation follows a path through the deeper material that is on the lift side of the screw conveyor. A generally vertical path is preferred. This is a direction of the radiation path, relative to flowing material, as shown in FIG. 2B of U.S. Pat. No. 3,518,425, for which linearization of the amplified detector output was found to be difficult.

It is an object of the present invention to provide improved monitoring by nuclear radiation means of the flow of particulate solids through a screw conveyor.

BRIEF DESCRIPTION OF THE DRAWING

A fuller understanding of the invention may be had by referring to the following description and claims, taken in conjunction with the accompanying drawing, in which:

DESCRIPTION OF THE PREFERRED EMBODIMENT

Figure 1:
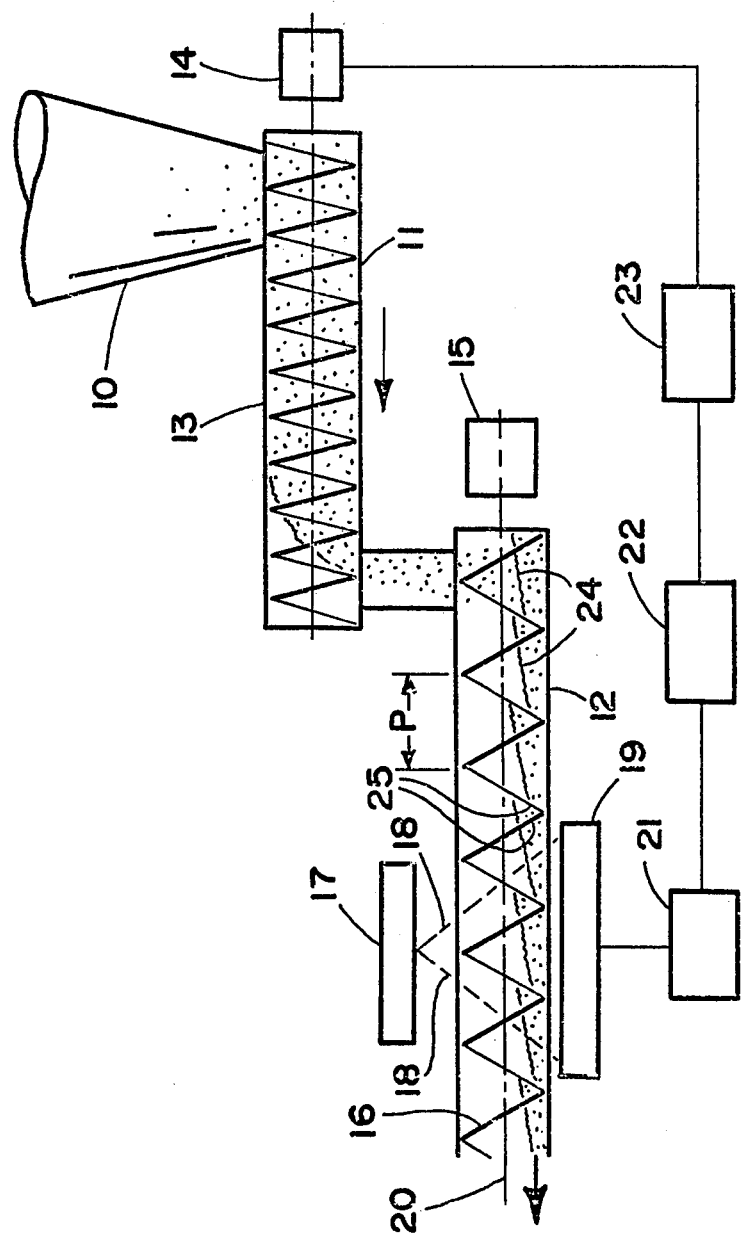
FIG. 1 represents an embodiment of the invention in which a variable speed screw feeder delivers material from a storage bin to discharge into a constant speed screw conveyor through which radiation is passed from an upper point source to a lower detector that extends parallel to the screw conveyor.

In the embodiment of the invention shown in FIG. 1, particulate solid material is delivered from storage bin 10 by screw feeder 11 to screw conveyor 12 through which it is carried to its place of use. Preferably, the material flows within a mass-flow system as described by A. W. Jenike and J. R. Johanson in *Mineral Science Engineering*, April, 1972, pages 3 to 13, and by G. Doeksen in *Journal of Engineering for Industry*, March, 1973. The screw of feeder 11 rotates at a speed slower than the critical speed at which the material becomes aerated or otherwise acts irregularly. Downstream sealing portion 13 of screw feeder 11 is normally filled to capacity. The screw of feeder 11 is driven by variable speed motor 14. Screw 16 of conveyor 12, which is only partially filled, rotates at a relatively high speed and is driven by constant speed motor 15. Screw 16 of conveyor 12 has uniform pitch P. Source 17 above screw conveyor 12 directs radiant energy in a beam bounded by broken lines 18 through screw conveyor 12 so that radiation that is not absorbed or scattered by the particulate solids or screw conveyor strikes detector 19 which is located below screw conveyor 12 and extends parallel to shaft 20 of screw 16 for a distance at least about equal to pitch P. Detector 19 is kept in spaced relationship with source 17. It is on the lift side of shaft 20, i.e., to the left for clockwise rotation or to the right for counterclockwise rotation when viewed in the direction of material flow. This is shown in the end view in FIG. 2. Radiation from source 17 to detector 19 is directed in a generally vertical path following a plane that is parallel to shaft 20 and that lies between the shaft and the conveyor casing on the lift side of the screw. An electrical signal is carried from detector 19 to preamplifier-linearizer 21 and thence to amplifier 22 and recorder 23 which may be provided with means, now shown, for controlling the speed of feeder motor 14. In one example of this embodiment, conveyor screw 16 had a pitch of 12 inches and detector 19 was 24 inches long, causing radiation received by the detector to pass through material within at least one pitch length of the screw. Means for transmission of the detector signal to the recorder are well known.

Figure 2:
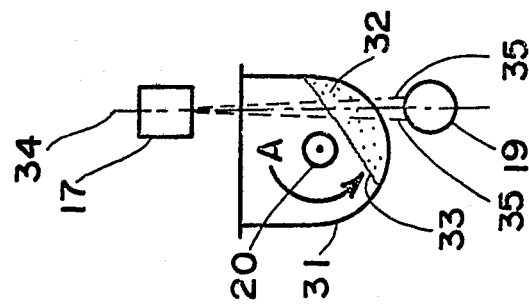
FIG. 2 shows an end view of a screw conveyor with radiation source and detector mounted in operating position.

In the end view, as shown in the example illustrated by FIG. 2, screw shaft 20 is represented by a circle within casing 31 and the direction of rotation of the screw is shown by arrow A. As a bed of particulate material 32 is being conveyed in a horizontal direction by the screw, its surface will be inclined in the direction of line 33. Radiation from source 17 is directed along operational centre line 34 towards detector 19, which is vertically disposed below source 17. Source 17 and detector 19 are placed in a plane about midway between shaft 20 and the side wall of casing 31 on the lift side of the screw to ensure that the radiation beam that is received by detector 19, bounded by plane shown as broken lines 35, passes through a deep portion of the bed without being intercepted by screw shaft 20. With this arrangement, radiation absorbed by material in the bed is relatively greater in comparison with that absorbed by the apparatus with other arrangements, such as in a plane on the opposite side of the screw.

The following example illustrates in more detail the operation of our invention on a screw conveyor that was used to monitor the flow of up to 100 metric tons per hour of particulate zinc calcine from a screw feeder to a reaction vessel. The screw feeder provided mass-flow delivery of calcine from bin 10 into the upstream charging end of a screw conveyor at a rate that was determined by the speed of rotation of the screw feeder drive motor. These features are shown in FIG. 1. A Nuclear Chicago Corporation Model No. 5093 instrument comprising radiation source 17 and radiation detector 19 was placed about a downstream portion of screw conveyor 12. The calcine was moved by 17 inch diameter screw 16 within a 19 inch high casing 31. The screw feeder was capable of delivering up to 100 metric tons per hour of zinc calcine. Pitch P of screw 16 was 16 inches. Point source 17 was 4 inches above the top of casing 31 and detector 19 was one half inch below the casing. Detector 19 was about 48 inches long and about 6 inches in diameter and it extended parallel to screw shaft 20. Since the length of detector 19 was about 3 times the pitch of screw 16, radiation it received passed directly through about 3 pitch-length segments of flowing material. About 2 such pitch-length segments are shown in FIG. 1, each segment having an upper surface that inclines downwardly in the direction of flow through the conveyor. Lines 24 represent the surfaces of portions of pitch-length segments that pass through boundaries 35 of FIG. 2. With counterclockwise rotation of shaft 20 as viewed from motor 15, these segment portions are behind the shaft. Immersed portions 25 of the blade of screw 16 push the material. When scanned by a narrow radiation beam that is at right angles to shaft 20, successive pitch-length variations in material depth, which are inherent in screw operation, are detected by the nuclear weightometer. Electronic averaging is required to eliminate recording of the cyclic irregularities. In the scanning of one or more pitch lengths of material, as shown in FIG. 1, through a longitudinal section of material that is relatively deep, as shown in FIG. 2, the mechanical arrangement provides detector 19 with an averaged signal, eliminating cyclic variations due to depth differentials within each screw pitch length. We have observed that, although all the material that passes through the screw conveyor does not pass through the radiation beam that is received by detector 19, our method monitors a representative sample of the flowing material. Since, in the example, conveyor screw 16 was operated at constant speed, a tachometer was not required to obtain integrated speed and detector signals.

In some situations, such as locations in which there is not sufficient room to install a separate conveyor, our nuclear weightometer apparatus may be used to monitor flow of material through a screw feeder. The radiation source and detector are installed on the downstream sealing portion 13 of screw feeder 11 in the same way as is shown for the screw conveyor in FIG. 1. As previously stated for the screw conveyor, it is essential that the screw in sealing portion 13 have constant pitch. With effective mass-flow discharge of bin 10, the sealing portion remains full of material during continuous operation. Under these conditions, the screw operates at a fixed percentage, depending on efficiency factors such as slippage of the material it is handling, of its theoretical capacity for a set speed of rotation. A nuclear weightometer on the screw feeder provides rapid detection of malfunctioning of the mass-flow system such as holdup of material, in which case the conveying part of the feeder is only partially filled and the detector signal changes accordingly. A screw feeder installation, however, does not detect flooding, a condition in which material moves through the feeder faster than it can be carried by the action of the screw itself.

Mechanical averaging of cyclic variations in radiation signals as tapered pitch-length segments of material move through the conveyor substantially reduces the need for electronic averaging of signals received by the detector. However, with flowing material, there are always minor variations in the absorption of radiation present and some electronic averaging is desirable. We have operated with amplifier time constants of 2, 10 and 20 seconds, such time constants being defined as the time for a system output to reach 63.2 percent of its final value after a step change in input. A low time constant provides high sensitivity to feed rate change but there is also sensitivity to irrelevant signals. A high time constant provides smooth recording of signals but there is less rapid response to feed rate change. Use of a variable time constant instrument permits easy adjustment to meet downstream process requirements.

When used to monitor the flow of particulate material through a screw conveyor, the nuclear weightometer arrangement of the present invention not only detects minor irregularities in operation of the variable speed screw feeder but also indicates when flooding of material through the feeder occurs. This material flows into and only partially fills casing 31 of the more rapidly rotating conveyor screw. We have found, by dynamic tests, good linear correlations, within one percent for one minute samples, between feeder rates and nuclear weightometer outputs for screw conveyor loadings between 2 and 17 percent of capacity. Static measurements for up to 30 percent loadings were in good agreement. With more than about 60 percent of capacity in a screw conveyor and less than about 80 percent capacity in a screw feeder, the material tends to drop back on turning of the screw, causing irregular changes in feeder or conveyor efficiency. In operation, the nuclear weightometer recorder is calibrated to give a full scale reading for a flow equal to the capacity of the screw feeder. It responds quickly to flooding of material through the feeder by showing very rapid increase in scale reading within a period determined by the time constant. Early detection of screw feeder flooding is an important factor in avoiding serious process control problems.

What we claim as new and desire to protect by Letters Patent of the U.S. is:

1. Apparatus for monitoring the flow of particulate solids through a screw conveyor comprising a radiation source and a radiation detector disposed about said conveyor, an amplifier and a recorder, said source and detector being placed in fixed relationship one above and one below the screw conveyor so that radiation from the source passes in a path into a bed of particulate solids moving through the conveyor and a substantial portion of said radiation, that is not absorbed or scattered by the solids or the screw conveyor, is received by the detector, said path being on the lift side of the conveyor screw, said path not being intercepted by the shaft of said screw, said detector extending parallel to the shaft of the screw for a distance at least about equal to the pitch of the screw, and said recorder receiving amplified electrical signals from said detector.

2. Apparatus as claimed in claim 1, said screw conveyor having a screw feeder operable by a variable speed motor in communication with and responsive to said amplified electrical signals to feed said screw conveyor at a determined rate whereby said screw conveyor is filled to not more than about 60 percent of its capacity by maximum flow, without flooding, from said screw feeder.

3. Apparatus for monitoring the flow of particulate solids through a screw feeder that is attached to a bin for the discharge of particulate solids therefrom, said apparatus comprising a radiation source and a radiation detector disposed about the downstream sealing portion of said screw feeder, an amplifier and a recorder, said source and detector being placed in fixed relationship one above and one below the casing surrounding said downstream sealing portion so that radiation from the source passes in a generally vertical path into a bed of said particulate solids and a substantial portion of said radiation, that is not absorbed or scattered by the solids or the screw feeder, is received by the detector, said path being on the lift side of the feeder screw, said path not being intercepted by the shaft of said screw, said detector extending parallel to the shaft of the screw for a distance at least about equal to the pitch of the screw, and said recorder receiving amplified electrical signals from said detector.

4. Apparatus as claimed in claim 3, said amplified electrical signals being used to control said flow of particulate solids by controlling the speed of said screw feeder.

5. A method of monitoring the flow of solids through a screw conveyor which comprises feeding particulate solids into the charging end of said conveyor to form a bed of solids moving in a horizontal direction within said conveyor, passing radiation from a source in a generally vertical path into said bed of particulate solids, receiving a substantial portion of said radiation, that is not absorbed or scattered by the solids or the screw conveyor, by a detector, and transmitting amplified electrical signals from the detector to a recorder, which method also comprises placing said source and detector in a spaced relationship one above and one below the screw conveyor with said path following a plane that is parallel to the shaft of the screw for a distance at least about equal to the pitch of the screw, said path being between the shaft and the conveyor casing on the lift side of the screw.

* * * * *